United States Patent
Takemoto et al.

(10) Patent No.: US 11,590,287 B2
(45) Date of Patent: Feb. 28, 2023

(54) NEEDLE-EQUIPPED OUTER CYLINDER AND METHOD FOR MANUFACTURING THE SAME

(71) Applicant: TERUMO KABUSHIKI KAISHA, Tokyo (JP)

(72) Inventors: Masafumi Takemoto, Shizuoka (JP); Fumiya Matsumoto, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 648 days.

(21) Appl. No.: 16/586,190

(22) Filed: Sep. 27, 2019

(65) Prior Publication Data

US 2020/0023133 A1  Jan. 23, 2020

Related U.S. Application Data

(63) Continuation of application No. PCT/JP2018/010345, filed on Mar. 15, 2018.

(30) Foreign Application Priority Data

Mar. 31, 2017  (JP) .............................. JP2017-071528

(51) Int. Cl.
*A61M 5/28* (2006.01)
*A61M 5/34* (2006.01)
(Continued)

(52) U.S. Cl.
CPC ................ *A61M 5/28* (2013.01); *A61M 5/34* (2013.01); *A61M 5/3202* (2013.01);
(Continued)

(58) Field of Classification Search
CPC ........ A61M 5/28; A61M 5/34; A61M 5/3202; A61M 5/3134; A61M 5/349; A61M 5/343;
(Continued)

(56) References Cited

U.S. PATENT DOCUMENTS 3,728,184 A * 4/1973 Burke ................. B29C 65/0672
156/73.1
5,810,782 A * 9/1998 Saito ..................... A61M 5/322
604/110
(Continued)

FOREIGN PATENT DOCUMENTS

CN     103906540 A     7/2014
CN     105682720 A     6/2016
(Continued)

OTHER PUBLICATIONS

International Searching Authority, "International Search Report" and "Written Opinion" issued in connection with International Patent Application No. PCT/JP2018/010345, dated May 15, 2018.
(Continued)

*Primary Examiner* — Tasnim Mehjabin Ahmed
(74) *Attorney, Agent, or Firm* — Foley & Lardner LLP

(57) ABSTRACT

A needle-equipped outer cylinder includes: a needle tube; a joining member comprising: a needle tube accommodation hole that accommodates a proximal end side portion of the needle tube and penetrates the joining member from a distal end of the joining member to a proximal end of the joining member, and a joining outer peripheral portion provided on an outer peripheral portion of the needle tube accommodation hole; and an outer cylinder member comprising: a distal end joint that comprises an inner cavity that receives the joining outer peripheral portion of the joining member from a distal end side, and a projection located at a proximal end portion of the inner cavity and projecting into the inner cavity. The joining member comprises, at a proximal end portion of the joining member, an abutment portion that abuts the projection of the outer cylinder member.

11 Claims, 13 Drawing Sheets

(51) Int. Cl.
    *A61M 5/32*     (2006.01)
    *A61M 5/31*     (2006.01)
    *B29C 65/50*     (2006.01)
    *B29L 31/00*     (2006.01)

(52) U.S. Cl.
    CPC ... *A61M 2005/312* (2013.01); *A61M 2207/00* (2013.01); *B29C 65/5057* (2013.01); *B29L 2031/7544* (2013.01)

(58) Field of Classification Search
    CPC .......... A61M 2005/312; B29C 65/5057; B29L 2031/7544
    See application file for complete search history.

(56) References Cited

U.S. PATENT DOCUMENTS

| | | | |
|---|---|---|---|
| 2002/0138042 A1 | 9/2002 | Llorach et al. | |
| 2008/0187697 A1* | 8/2008 | Amano | B29C 66/54 156/272.8 |
| 2015/0165134 A1* | 6/2015 | Hoppe | A61M 5/343 604/240 |
| 2015/0374931 A1* | 12/2015 | Sugiki | A61M 5/343 604/240 |

FOREIGN PATENT DOCUMENTS

| | | |
|---|---|---|
| EP | 2 965 774 A1 | 1/2016 |
| JP | 2004-154210 A | 6/2004 |
| JP | 2005-342100 A | 12/2005 |
| JP | 2006-247892 A | 9/2006 |
| JP | 2007-253416 A | 10/2007 |
| WO | WO-2014/136239 A1 | 9/2014 |

OTHER PUBLICATIONS

Extended European Search Report dated Aug. 11, 2020 in corresponding European Patent Application No. 18777530.9.

International Searching Authority, "International Search Report," issued in connection with International Patent Application No. PCT/JP2018/010345, dated May 15, 2018.

International Searching Authority, "Written Opinion," issued in connection with International Patent Application No. PCT/JP2018/010345, dated May 15, 2018.

Chinese First Office Action issued on Application No. 201880022898.9 dated Apr. 2, 2021.

\* cited by examiner

NEEDLE-EQUIPPED OUTER CYLINDER AND METHOD FOR MANUFACTURING THE SAME

CROSS-REFERENCE TO RELATED APPLICATIONS

This is a bypass continuation of PCT Application No. PCT/JP2018/010345, filed on Mar. 15, 2018, which claims priority to Japanese Application No. 2017-071528, filed on Mar. 31, 2017. The contents of these applications are hereby incorporated by reference in their entireties.

BACKGROUND

The present disclosure relates to a needle-equipped outer cylinder in which a needle tube of an injector is directly fixedly joined to a distal end of an injector outer cylinder in advance, a method for manufacturing the same, and a prefilled syringe using the needle-equipped outer cylinder.

In a case of an injector with a small volume used for insulin administration, vaccine administration and the like, a needle-equipped outer cylinder in which a needle tube of the injector is fixedly joined directly to a distal end of an injector outer cylinder in advance is sometimes used. As a method for manufacturing such needle-equipped outer cylinder, in addition to a method for joining the needle tube to the distal end of the outer cylinder with an adhesive or the like and a method for joining the needle tube to the distal end portion of the outer cylinder by insert molding, a method for heat-welding the needle tube to the outer cylinder is known (refer to JP 2005-342100 A). A method in which a cylindrical joining member is interposed between the needle tube and the outer cylinder, and the joining member is press-fitted to the outer cylinder, thereby assembling the three members is also known (refer to JP 2004-154210 A).

SUMMARY

In a case of using the joining member as in JP 2005-342100 A and JP 2004-154210 A, as a method for heat-welding the joining member and the outer cylinder, it is preferable to heat-weld a tapered portion and a tapered inner cavity while pressing the joining member in a proximal end side direction thereof with respect to the outer cylinder by using the joining member including the tapered portion an outer diameter of which is reduced from a distal end side toward a proximal end side and the outer cylinder provided with a distal end joint including the tapered inner cavity capable of receiving the tapered portion of the joining member. At this heat-welding step, it is not necessary to heat-weld an entire contact surface between the joining member and the outer cylinder, and it is sufficient that an annular heat-welded part is formed. Therefore, a part of the outer cylinder that abuts the joining member has a non-heat-welded portion that is not heated to temperature equal to or higher than a softening point and is not heat-welded to the joining member.

Also, at the heat-welding step, when the entire joining member is heated to a certain level or more, even a site on the distal end side of the joining member not inserted into the tapered inner cavity of the outer cylinder could be softened to be deformed to have an outer diameter larger than an inner diameter of an opening of the tapered inner cavity. When such deformation occurs, the deformed portion cannot enter the tapered inner cavity. For this reason, it becomes difficult to heat-weld while pressure bonding the surfaces of the tapered portion and the tapered inner cavity to each other, and it becomes difficult to improve reliability of welding between the joining member and the outer cylinder.

Therefore, it is desirable to limit a heated range so as to sufficiently heat to ensure heat-welding in a portion other than a distal end such as an intermediate portion of the joining member, whereas the site on the distal end side of the joining member is not softened. In such circumstances, an outer cylinder of a portion abutting the joining member has a portion that abuts but is a non-heat-welded portion. There has been a problem that crack occurs in the portion that is an abutment portion and the non-heat-welded portion after manufacture of the needle-equipped outer cylinder.

Therefore, the applicant of the present application has proposed a configuration described in WO2014/136239 (US2015-374931, EP2965774).

In WO2014/136239, a needle-equipped outer cylinder 1 includes a needle tube 3, a joining member 4 including a needle insertion hole 42 penetrating from a distal end to a proximal end into which the needle tube 3 is inserted and a tapered portion 47 an outer diameter of which is reduced from a distal end side toward a proximal end side, and an outer cylinder member 2 provided with a distal end joint 22 including a tapered inner cavity 26 capable of receiving the tapered portion 47 of the joining member 4. The joining member 4 is inserted into the inner cavity 26 of the distal end joint 22 of the outer cylinder member 2 and is fixed to the distal end joint 22 by a heat-welded portion 45 formed in a position on a proximal end side by a predetermined length from a distal end of the distal end joint 22. The distal end joint 22 includes a non-welded abutment portion 46 that is a non-heat-welded portion and abuts the joining member 4 on a site on the distal end side of the heat-welded portion 45. The non-welded abutment portion 46 has residual strain and does not have crack.

The one disclosed in WO2014/136239 has a sufficient effect. However, there is a case in which a molding difference occurs in an outer cylinder member 2 and a joining member 4 that are moldings. In a case in which this occurs in the tapered portion of the joining member and the tapered inner cavity of the distal end joint of the outer cylinder, when the joining member is inserted into the distal end joint of the outer cylinder member, it is possible that the joining member is not sufficiently fixed in the distal end joint, and a joint between the joining member and the outer cylinder by heat-welding is not stable.

Embodiments of the present invention have been developed in view of the above-described problems.

Embodiments of the present disclosure include a needle-equipped outer cylinder including a needle tube, a joining member including a needle tube accommodation hole that penetrates from a distal end to a proximal end into which the needle tube is inserted and a tapered portion an outer diameter of which is reduced from a distal end side toward a proximal end side, and an outer cylinder member provided with a distal end joint including an inner cavity capable of receiving the tapered portion of the joining member in which the joining member is excellently fixedly joined to the outer cylinder member; a method for manufacturing the same; and a prefilled syringe using the needle-equipped outer cylinder.

According to one embodiment, a needle-equipped outer cylinder includes: a needle tube; a joining member including a needle tube accommodation hole for accommodating a proximal end side portion of the needle tube and a joining outer peripheral portion provided on an outer peripheral portion of the needle tube accommodation hole; and an outer cylinder member provided with a distal end joint including an inner cavity capable of receiving the joining outer peripheral portion of the joining member from a distal end side. The needle tube accommodation hole penetrates the joining member from a distal end of the joining member to a proximal end of the joining member. The outer cylinder member is provided with a projection provided on a proximal end portion of the inner cavity and projecting in the inner cavity. The joining member is provided with an abutment portion that abuts the projection of the outer cylinder member on a proximal end portion of the joining member. At least the joining outer peripheral portion of the joining member is inserted into the inner cavity of the distal end joint of the outer cylinder member. The abutment portion of the joining member abuts the projection of the outer cylinder member. The joining outer peripheral portion of the joining member includes a heat-welded portion formed in a position on a proximal end side by a predetermined length from a distal end of the distal end joint of the outer cylinder member. The joining outer peripheral portion of the joining member is fixedly joined to an inner peripheral surface of the distal end joint on an outer peripheral portion of the heat-welded portion and is fixedly joined to an outer peripheral surface of the needle tube on an inner peripheral portion of the heat-welded portion.

According to another embodiment, a method is provided for manufacturing a needle-equipped outer cylinder provided with a needle tube, a joining member including a needle tube accommodation hole for accommodating the needle tube and a joining outer peripheral portion provided on an outer peripheral portion of the needle tube accommodation hole, and an outer cylinder member provided with a distal end joint including an inner cavity capable of receiving the joining outer peripheral portion of the joining member. The method for manufacturing the needle-equipped outer cylinder includes: a preparing step of preparing the outer cylinder member provided with a projection projecting in the inner cavity on a proximal end portion of the inner cavity, the joining member provided with an abutment portion that abuts the projection of the outer cylinder member on a proximal end portion, and the needle tube; an assembling step of assembling the needle tube, the joining member, and the outer cylinder member such that the needle tube is inserted into or inserted to be fixed to the needle tube accommodation hole of the joining member, the joining member is inserted into the distal end joint of the outer cylinder member, and the abutment portion of the joining member abuts the projection of the outer cylinder member; and a welding step of heat-welding the joining outer peripheral portion of the joining member to an inner peripheral surface of the distal end joint of the outer cylinder member and an outer peripheral surface of the needle tube by allowing the needle tube to generate heat by a heat generating device to allow the needle tube to generate heat while pressing a distal end portion of the joining member in a proximal end direction of the joining member by a pressing member.

DETAILED DESCRIPTION

Figure 1:
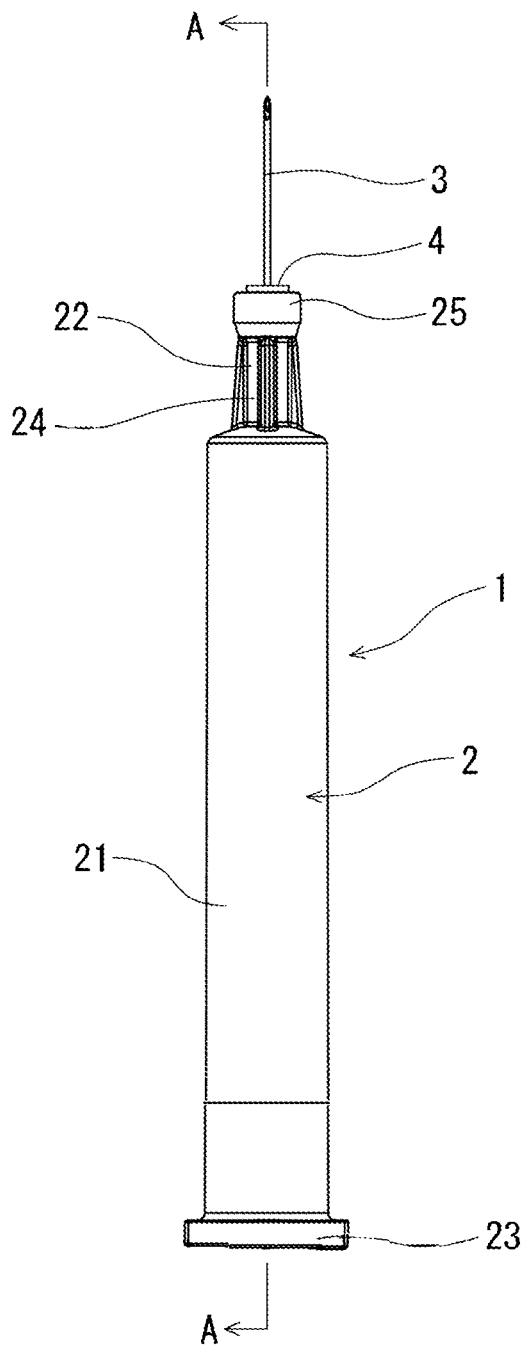
FIG. 1 is a front view of a needle-equipped outer cylinder according to an embodiment of the present invention.
Figure 2:
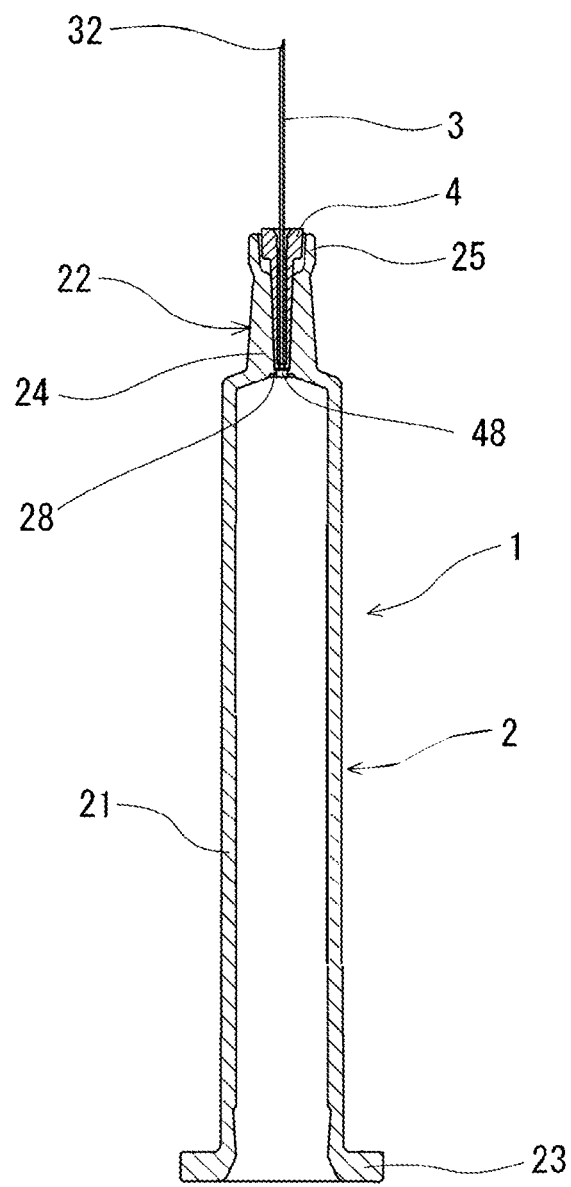
FIG. 2 is a cross-sectional view taken along line A-A of the needle-equipped outer cylinder of FIG. 1.

Hereinafter, a needle-equipped outer cylinder according to embodiments of the present invention is described with reference to the drawings.

According to one embodiment, a needle-equipped outer cylinder 1 includes a needle tube 3, a joining member 4 including a needle tube accommodation hole 42 for accommodating a proximal end side portion of the needle tube 3 and a joining outer peripheral portion 47 provided on an outer peripheral portion of the needle tube accommodation hole 42 (in other words, arranged around an axis), and an outer cylinder member 2 provided with a distal end joint 22 including an inner cavity 26 capable of receiving the joining outer peripheral portion of the joining member 4 from a distal end side. The needle tube accommodation hole 42 penetrates the joining member 4 from a distal end of the joining member 4 to a proximal end of the joining member 4.

The outer cylinder member 2 is provided with a projection 28 arranged on a proximal end portion of the inner cavity 26 and projecting in the inner cavity 26. The joining member 4 is provided with an abutment portion 48 that abuts the projection 28 of the outer cylinder member 2 on a proximal end portion of the joining member 4. At least the joining outer peripheral portion 47 of the joining member 4 is inserted into the inner cavity 26 of the distal end joint 22 of the outer cylinder member 2, and the abutment portion 48 of the joining member 4 abuts the projection 28 of the outer cylinder member 2.

The joining outer peripheral portion 47 of the joining member 4 includes a heat-welded portion 45 formed in a position on a proximal end side by a predetermined length from a distal end of the distal end joint 22 of the outer cylinder member 2. The joining outer peripheral portion 47 of the joining member 4 is fixedly joined to an inner peripheral surface of the distal end joint 22 on an outer peripheral portion of the heat-welded portion 45 and is fixedly joined to an outer peripheral surface of the needle tube 3 on an inner peripheral portion of the heat-welded portion 45.

The needle-equipped outer cylinder according to embodiments of the present invention may be used for tapping a needle tip from a surface of the skin and injecting medicine solution into a living body.

Figure 10:
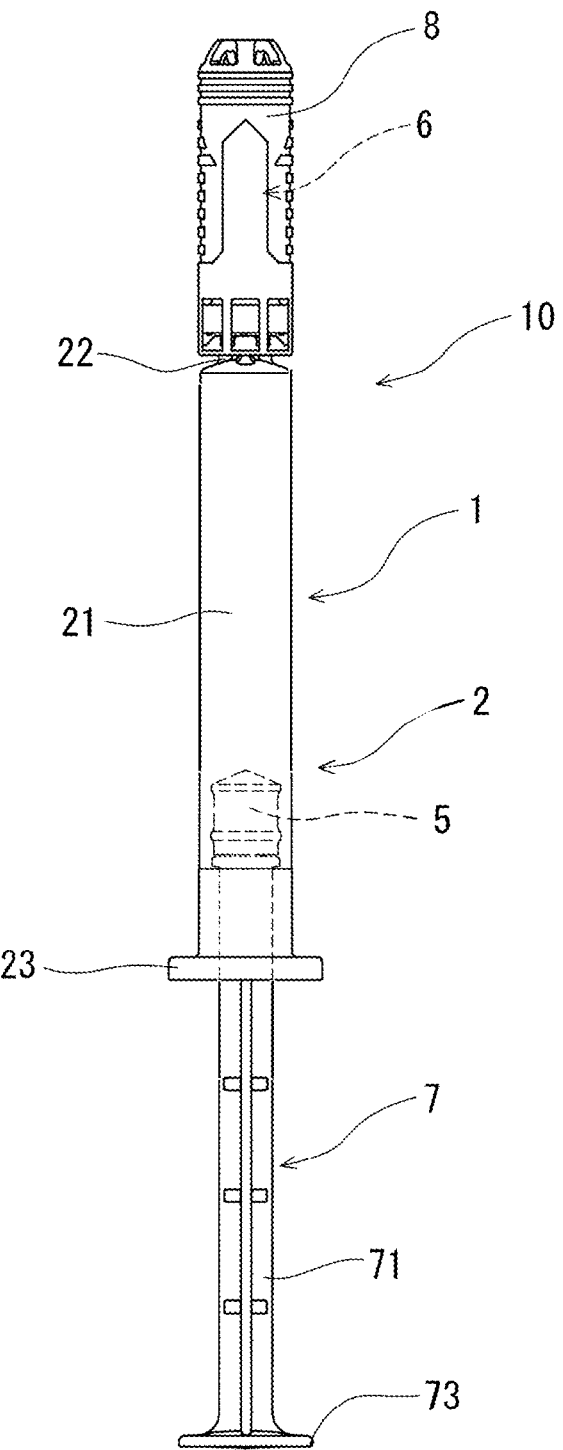
FIG. 10 is a front view of a prefilled syringe using the needle-equipped outer cylinder according to an embodiment of the present invention.
Figure 11:
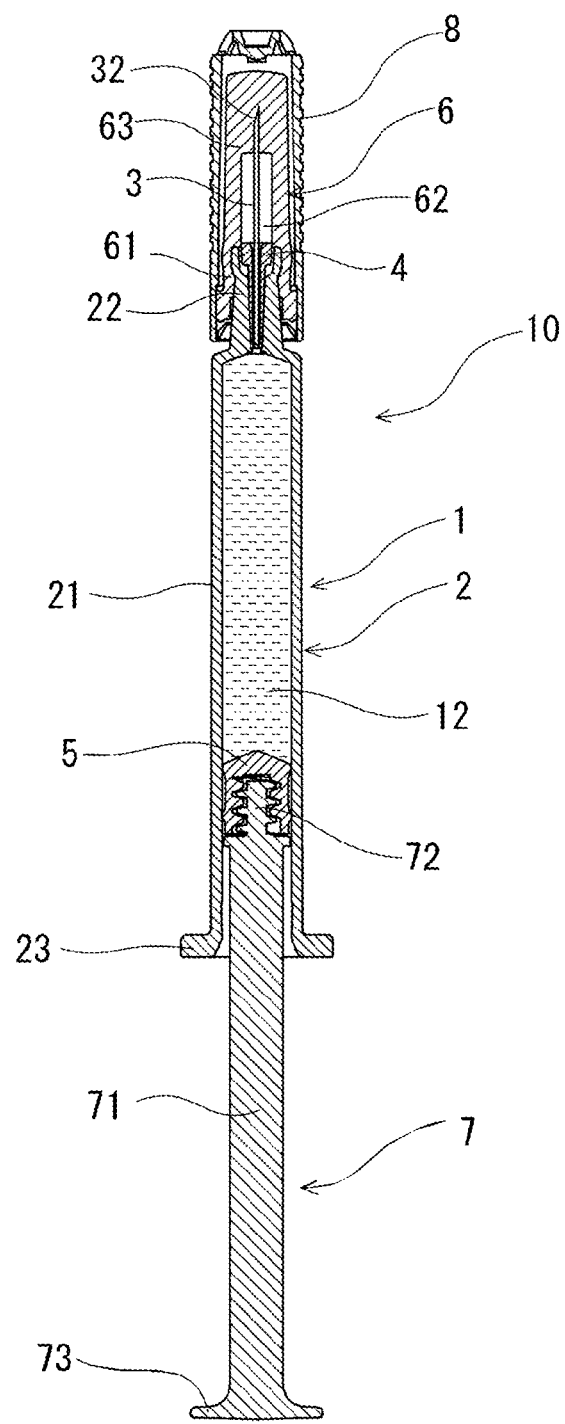
FIG. 11 is a longitudinal cross-sectional view of the prefilled syringe of FIG. 10.

As illustrated in FIG. 1 to FIG. 4, the needle-equipped outer cylinder 1 of this example is provided with the needle tube 3, the joining member 4 to which the needle tube 3 is fixedly joined, and the outer cylinder member 2 to which the joining member 4 is fixedly joined. Also, as illustrated in FIGS. 10 and 11, a cap 6 is attached to the needle-equipped outer cylinder 1.

Figure 3:
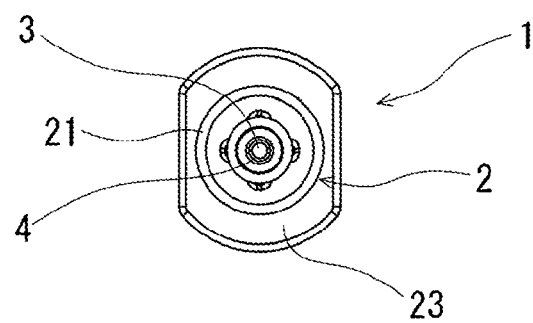
FIG. 3 is a plan view of the needle-equipped outer cylinder of FIG. 1.
Figure 9:
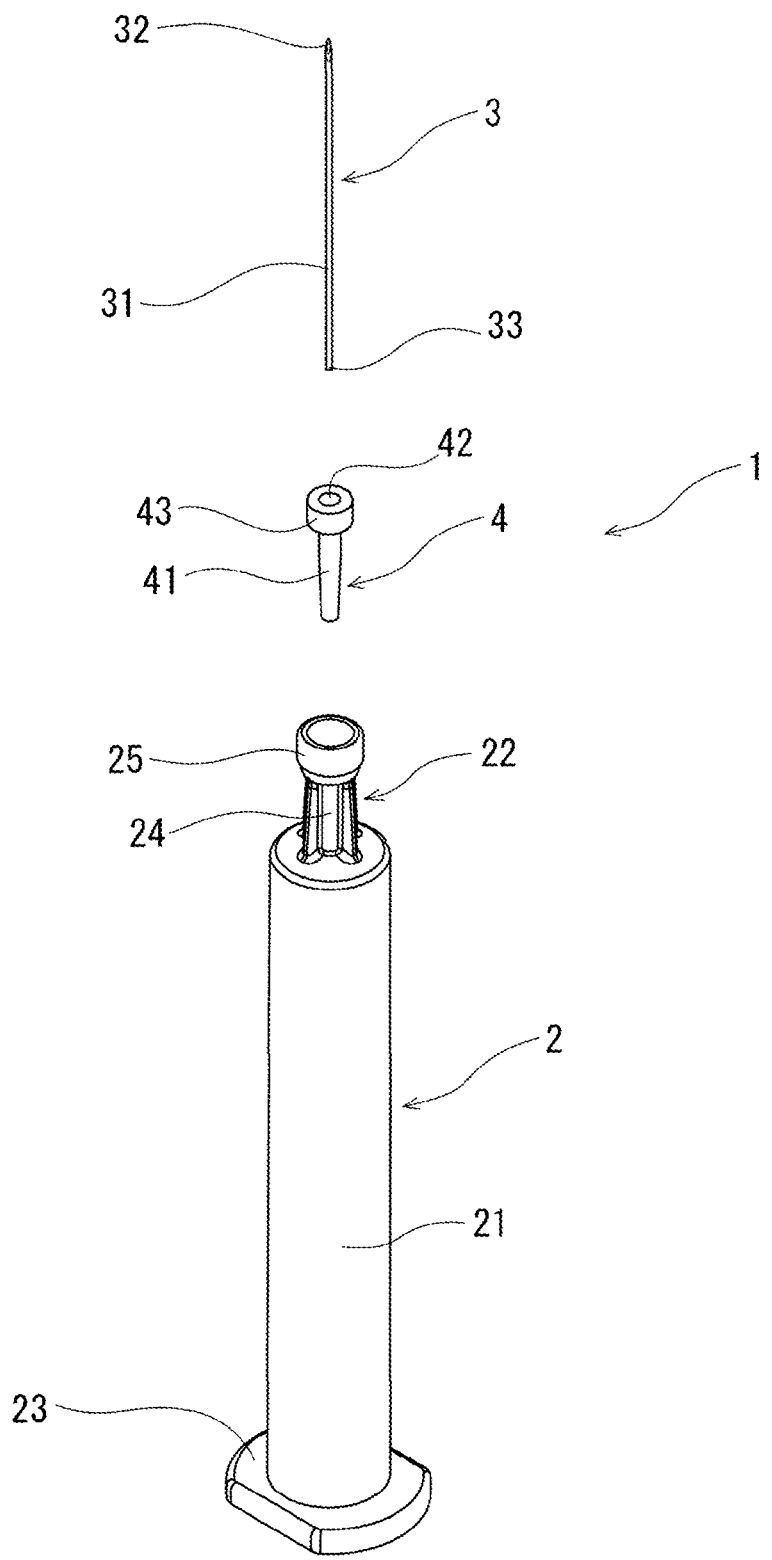
FIG. 9 is an exploded perspective view of the needle-equipped outer cylinder according to an embodiment of the present invention.

As illustrated in FIGS. 1, 3, and 9, the needle tube 3 of 27 to 30 G (outer diameter: φ0.41 to 0.31 mm) according to the ISO standards for medical needle tube (ISO9626:1991/Amd.1:2001(E)) is used. Note that, a size of the needle tube 3 may be 26 G or larger.

On one end in an axial direction of the needle tube 3, a needle tip 32 to be tapped into the living body is formed. The needle tip 32 is formed at an acute angle with a blade surface. The needle tube 3 is formed to have a length such that the needle tip 32 thereof projects from a distal end side cylinder portion (distal end portion) 43 of the joining member 4, and a proximal end 33 of the needle tube 3 on the opposite side of the needle tip 32 projects from the joining outer peripheral portion 47 (in this example, tapered portion) 47 of the joining member 4 to be arranged in the distal end joint 22 of the outer cylinder member 2.

An intermediate portion 31 of the needle tube 3 is inserted into the needle tube accommodation hole 42 of the joining member 4. A surface of at least the intermediate portion 31 in the needle tube 3 is made a rough surface by blasting or the like. As a result, when the needle tube 3 and the joining member 4 are joined by heat-welding, a softened resin enters unevenness of the rough surface of the needle tube 3 and may improve joining strength between the needle tube 3 and the joining member 4. Also, the softened resin enters the unevenness of the rough surface of the needle tube 3 and may improve liquid tightness.

As a material of the needle tube 3, for example, stainless steel is preferable. However, the material is not limited thereto, and aluminum, an aluminum alloy, titanium, a titanium alloy, and other metal may also be used. Also, not only a straight needle but also a tapered needle in which at least a part is tapered may be used as the needle tube 3. A cross-sectional shape of the needle tube 3 is not limited to a circle, but may be a polygon such as a triangle. A coating agent made of, for example, a silicone resin or a fluorine-based resin may be applied to the surface on the needle tip 32 side of the needle tube 3.

Next, the joining member 4 is described.

Figure 6:
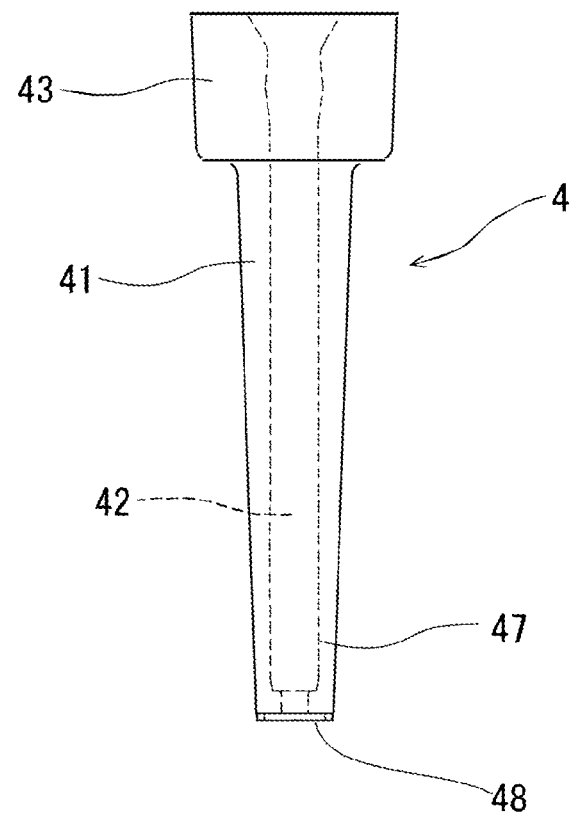
FIG. 6 is an enlarged front view of a joining member used in the needle-equipped outer cylinder according to an embodiment of the present invention.
Figure 7:
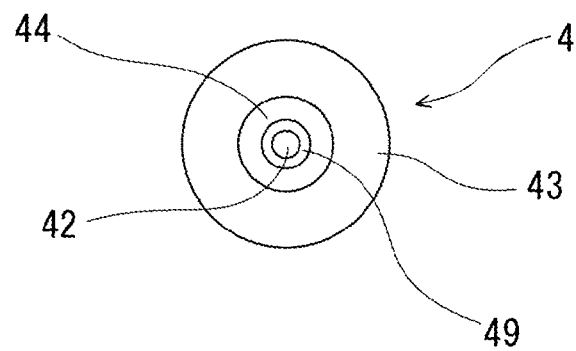
FIG. 7 is a plan view of the joining member of FIG. 6.
Figure 8:
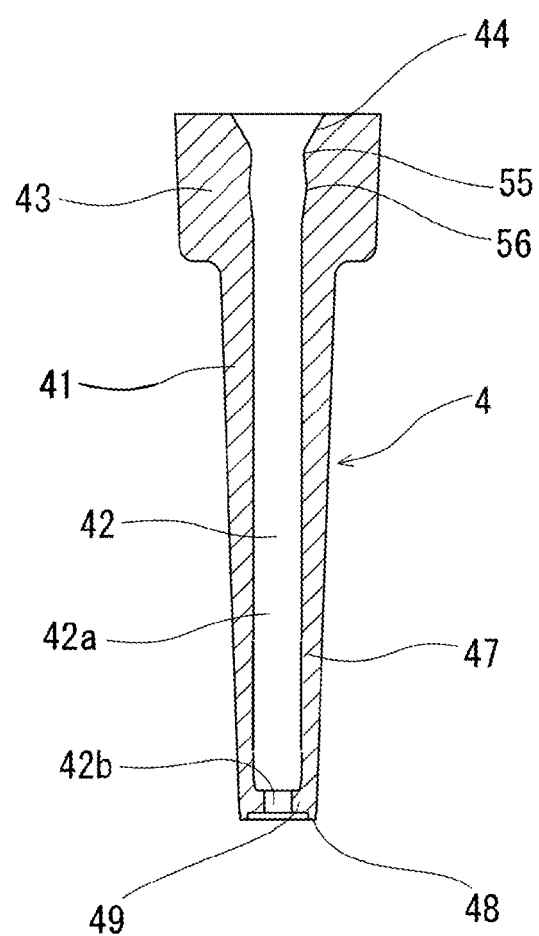
FIG. 8 is a longitudinal cross-sectional view of the joining member of FIG. 6.

As illustrated in FIGS. 6 to 8, the joining member 4 is formed of the distal end side cylinder portion (distal end portion) 43 and a proximal end side cylinder portion 41 having an outer diameter smaller than that of the distal end side cylinder portion 43 and is longer than the distal end side cylinder portion 43. The joining member 4 is provided with the needle tube accommodation hole 42 into which the needle tube 3 is inserted and the joining outer peripheral portion 47 formed on the outer peripheral portion thereof. The distal end side cylinder portion 43 is formed into a cylindrical shape having a substantially uniform outer diameter. In this example, an outer surface of the proximal end side cylinder portion 41, in other words, an outer surface of the joining outer peripheral portion 47, is formed into a tapered shape in which an outer diameter is continuously reduced toward the proximal end side of the joining member 4. Also, a cross-section in a radial direction of the joining outer peripheral portion 47 is formed into a circular shape, and preferably, in this embodiment, a substantially perfect circular shape.

The joining member 4 is provided with the abutment portion 48 that abuts the projection 28 provided on the proximal end portion of the inner cavity 26 of the outer cylinder member 2 as described below. In this example, the abutment portion 48 of the joining member 4 is formed of an annular rib projecting rearward from the proximal end (specifically, a proximal end surface) of the joining member 4. Note that, the abutment portion may be one or a plurality of ribs that is not annular. Furthermore, the abutment portion may be formed of the proximal end surface of the joining member 4 instead of providing the above-described rib. Also, the abutment portion may be formed of a projection or an annular concave portion provided on a side portion of the proximal end portion of the joining member 4.

The joining member 4 includes the needle tube accommodation hole 42 into which the needle tube 3 is inserted. The needle tube accommodation hole 42 includes a needle tube accommodating portion 42a for accommodating the proximal end side portion of the needle tube, and a communication hole 42b communicated with the needle tube accommodating portion 42a and surrounded by a needle tube locking portion 49 to be described below. A diameter of the needle tube accommodating portion 42a of the needle tube accommodation hole 42 is made larger than the outer diameter of the needle tube 3 by about 0.02 to 0.14 mm, preferably about 0.05 to 0.11 mm. In a case of using the above-described needle tube 3 of 27 to 30 G, by setting the diameter of the needle tube accommodating portion 42a to 0.43 to 0.45 mm, a gap with the needle tube 3 may be set as described above. By setting as described above, it is possible to secure the joining strength of the needle tube 3 after joint and prevent the needle tube 3 after joint from inclining by a predetermined amount or larger. Note that, in a case in which the needle tube of 26 G or larger is used, an inner diameter of the needle tube accommodating portion 42a is set to 0.46 mm or larger.

Also, a thickness from an outer surface of the joining member 4 to the needle tube accommodation hole 42 is set to 0.38 to 0.48 mm. By making such joining member 4, it is possible to manufacture the needle-equipped outer cylinder 1 by using a single joining member 4 and each needle tube 3 of 27 to 30 G while securing the joining strength of the needle tube 3, and preventing the needle tube 3 after joint from inclining by a predetermined amount or larger.

Also, as illustrated in FIG. 8, a distal end side portion of the needle tube accommodation hole 42 (inner portion of the distal end side cylinder portion 43) is an enlarged diameter portion 44, a diameter of which is enlarged as compared with other portions. Furthermore, on a proximal end of the enlarged diameter portion 44, an annular rib 55 that projects gently is formed. There are gentle inclined surfaces around an apex of the annular rib 55. Also, on a proximal end side of the annular rib 55, an annular concave portion 56 is provided.

Figure 4:
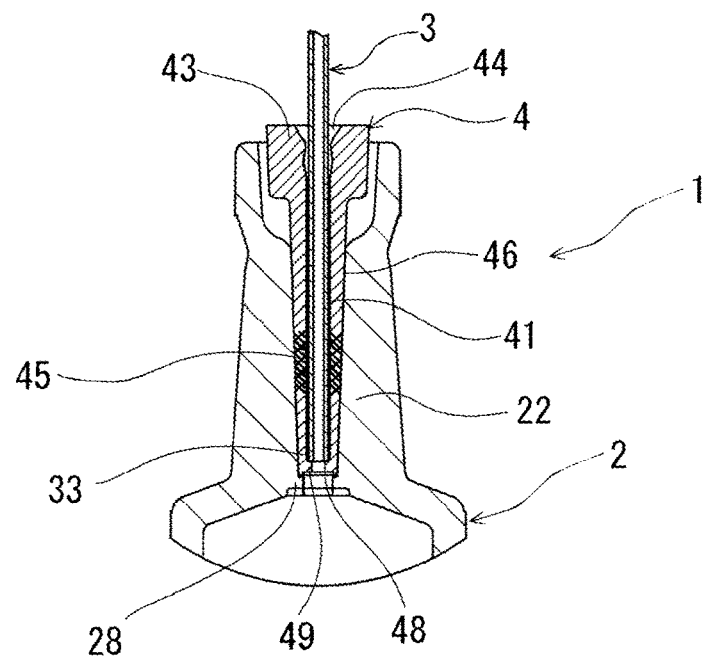
FIG. 4 is an enlarged longitudinal cross-sectional view of a distal end portion of the needle-equipped outer cylinder according to an embodiment of the present invention.

In the needle-equipped outer cylinder 1 of this example, as illustrated in FIGS. 4 and 8, the joining member 4 is provided with the needle tube locking portion 49 provided on a proximal end portion of the needle tube accommodation hole 42. As illustrated in FIG. 4, the proximal end 33 of the needle tube 3 inserted into the joining member 4 abuts the needle tube locking portion 49, and movement in a proximal end direction, in other words, removal from the joining member 4 is restricted. Therefore, a projecting length of the needle tube 3 from the distal end of the joining member 4 is constant.

In this example, the needle tube locking portion 49 is formed of an annular projection that projects from an inner surface of the needle tube accommodating portion 42a of the needle tube accommodation hole 42 of the joining member 4. In addition, it is preferable that the annular projection has a rising surface directed in a distal end direction with respect to the inner surface of the needle tube accommodating portion 42a. By such configuration, an abutment state with the proximal end 33 of the needle tube 3 is stabilized. However, the needle tube locking portion 49 may also be provided with, for example, an inclined surface a diameter of which is reduced in the proximal end direction. The needle tube locking portion 49 may be one or a plurality ribs that is not annular.

In this example, the needle tube locking portion 49 is provided on the proximal end of the needle tube accommodation hole 42. However, the needle tube locking portion 49 may also be located not on the proximal end of the needle tube accommodation hole 42 but distal of the proximal end by a predetermined length.

In addition, the needle tube accommodation hole 42 includes the communication hole 42b, a diameter of which is smaller than that of the needle tube accommodating portion 42a, surrounded by the needle tube locking portion 49. An inner portion of an outer cylinder main body 21 of the outer cylinder member 2 and the needle tube 3 are communicated with each other through the communication hole 42b. The diameter of the communication hole 42b is preferably larger than an inner diameter of the needle tube and smaller than the outer diameter of the needle tube. As a result, when the medicine solution filled in the outer cylinder main body 21 is discharged from the needle tube 3, the medicine solution may smoothly pass through the communication hole 42b.

Examples of forming materials of the joining member 4 and the outer cylinder member 2 include, for example, various resins such as polyvinyl chloride, polyethylene, polypropylene, cyclic polyolefin, polystyrene, poly-(4-methylpentene-1), polycarbonate, acrylic resin, acrylonitrile-butadiene-styrene copolymer, polyester such as polyethylene terephthalate, butadiene-styrene copolymer, and polyamide (for example, nylon 6, nylon 6.6, nylon 6.10, and nylon 12). Among them, resins such as polypropylene, cyclic polyolefin, polyester and poly-(4-methylpentene-1) are preferably used. It is preferable that the forming materials of the joining member 4 and the outer cylinder member 2 are substantially transparent in order to secure visibility of the inside.

Next, the outer cylinder member 2 is described.

Figure 5:
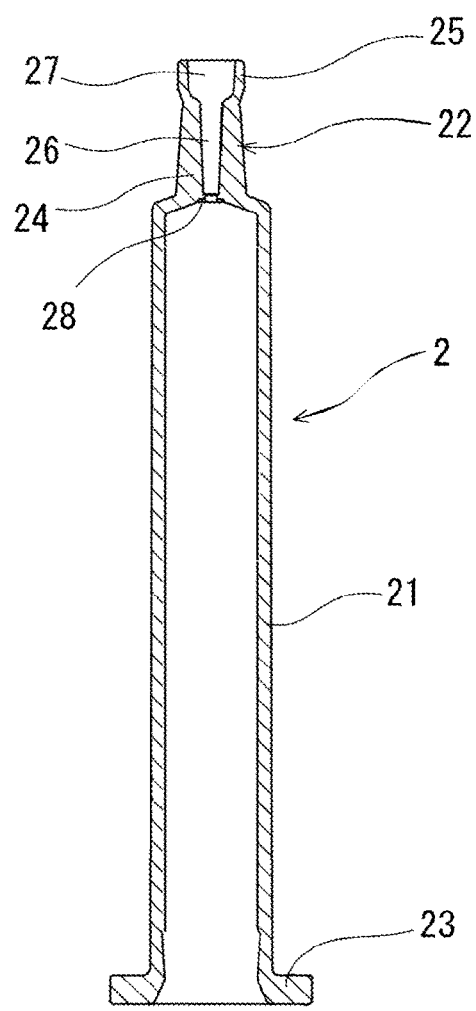
FIG. 5 is a longitudinal cross-sectional view of an outer cylinder member used in the needle-equipped outer cylinder according to an embodiment of the present invention.

As illustrated in FIG. 5, the outer cylinder member 2 is provided with the outer cylinder main body 21 filled with the medicine solution and the distal end joint 22 to which the joining member 4 is fixedly joined. The outer cylinder main body 21 is formed into a substantially cylindrical shape having an inner accommodating portion. A flange 23 is formed on a proximal end side in the axial direction of the outer cylinder main body 21. That is, the outer cylinder member 2 is a syringe outer cylinder member capable of being filled with the medicine solution.

The distal end joint 22 is formed of a joining member receiving portion 24 continuous to the outer cylinder main body 21, and a distal end side enlarged diameter portion 25 continuous to the joining member receiving portion 24. An outer shape of the joining member receiving portion 24 is formed such that a cross-section in a radial direction is substantially cruciform, that is, formed with four ribs extending in the axial direction. The inner cavity 26 for receiving the joining outer peripheral portion 47 of the joining member 4 from the distal end side is formed in the joining member receiving portion 24.

Figure 17:
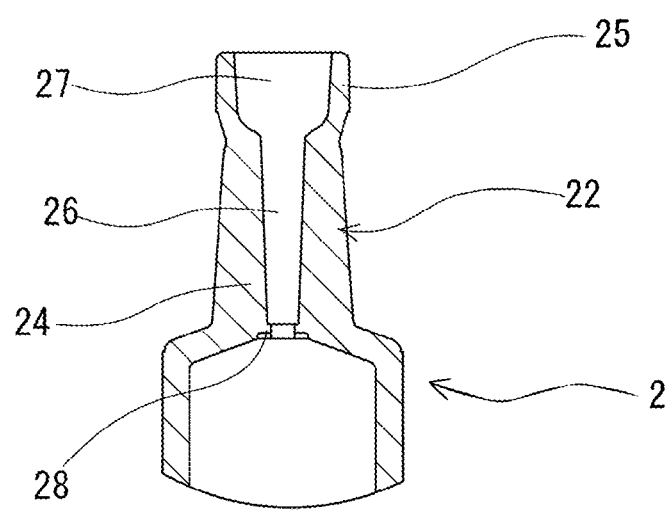
FIG. 17 is an enlarged cross-sectional view of the distal end portion of the outer cylinder member illustrated in FIG. 5.

The projection 28 provided on the proximal end portion of the inner cavity 26 is provided. In this example, the projection 28 is an annular projection projecting from an inner surface of the inner cavity 26. Also, the annular projection having a rising surface directed in the distal end direction with respect to the inner surface of the inner cavity 26 as that provided in the outer cylinder member 2 illustrated in FIGS. 4, 5, and 17 is preferable. By such configuration, the abutment state with the abutment portion (proximal end surface) of the joining member 4 is stabilized. However, the projection may also be provided with, for example, an inclined surface a diameter of which is reduced in the proximal end direction. A through hole is formed in the projection 28. Note that the projection may be one or a plurality of ribs that is not annular. In this example, the projection 28 is provided on a lower end of the inner cavity 26. However, the projection 28 may be located not on the lower end of the inner cavity 26 but on a distal end side by a predetermined length from the lower end. A projecting height of the projection 28 from the inner surface (inner surface near the projection) of the inner cavity 26 is preferably 0.03 to 0.35 mm, and more preferably 0.05 to 0.25 mm. Note that a projecting end of the projection 28 is preferably located on an inner peripheral side relative to an outer peripheral surface of the proximal end portion of the joining member and on an outer peripheral side relative to an inner peripheral surface of the needle tube locking portion 49 (communication hole 42b). As a result, when the medicine solution filled in the outer cylinder main body 21 is discharged from the needle tube 3, the medicine solution may smoothly pass through the inside of the projection 28.

In the needle-equipped outer cylinder 1 of this example, the joining outer peripheral portion (tapered portion) 47 of the joining member 4 is formed into substantially the same shape as the tapered shape of the tapered inner cavity 26 of the distal end joint 22 of the outer cylinder member 2. Therefore, the joining outer peripheral portion 47 is formed into a shape that may abut the tapered inner cavity 26 over substantially the entire surface in a state in which the abutment portion 48 (specifically, the proximal end surface) of the joining member 4 abuts the projection 28 of the inner cavity 26 of the outer cylinder member 2 when the joining outer peripheral portion 47 of the joining member 4 is inserted into the inner cavity 26 of the outer cylinder member 2. The cross-section in the radial direction of the tapered inner cavity 26 is formed into a circular shape, and preferably, in the outer cylinder of this example, is formed into a substantially perfect circular shape. Also, a thickness of a portion without the external rib of the joining member receiving portion 24 is preferably 0.5 to 2.0 mm, and more preferably 0.7 to 1.3 mm.

The tapered shapes of this tapered inner cavity 26 and joining outer peripheral portion 47 are substantially the same. Also, in the distal end side enlarged diameter portion 25, a distal end side cylinder portion accommodating portion 27 communicated with the tapered inner cavity 26 and accommodates the distal end side cylinder portion 43 of the joining member 4 is formed. The distal end side cylinder portion accommodating portion 27 is formed to have a diameter larger than that of a distal end of the tapered inner cavity 26. Taper angles of the tapered inner cavity 26 and the joining outer peripheral portion 47 of the joining member 4 are not particularly limited, but are preferably one to three degrees. As illustrated in FIG. 4, an inner diameter of the distal end side cylinder portion accommodating portion 27 is substantially the same as or slightly larger than an outer diameter of the distal end side cylinder portion 43 of the joining member 4 so that the distal end side cylinder portion 43 may be accommodated.

Figure 15:
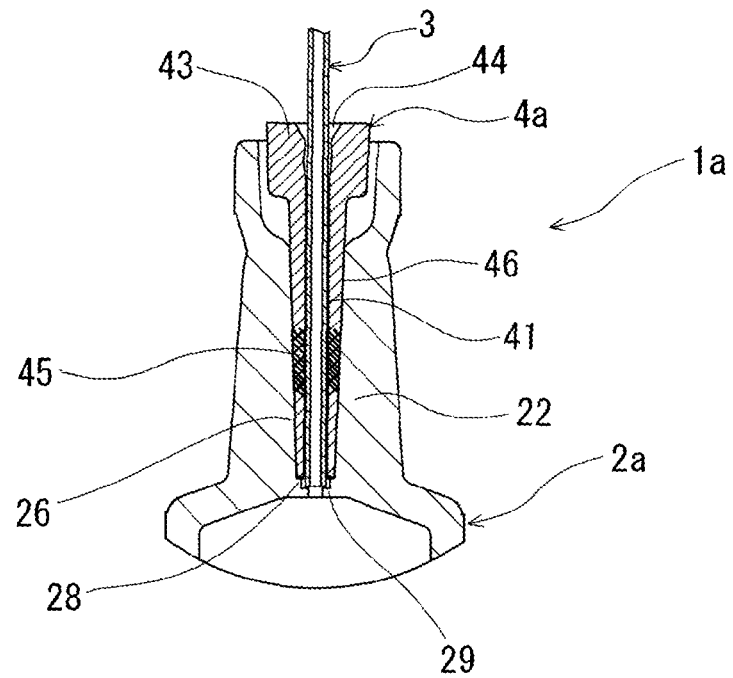
FIG. 15 is an enlarged longitudinal cross-sectional view of a distal end portion of the needle-equipped outer cylinder according to another example according to an embodiment of the present invention.

Also, in the needle-equipped outer cylinder 1 of this example, as illustrated in FIGS. 4 and 8 and described above, the joining member 4 is provided with the needle tube locking portion 49 provided on the proximal end portion of the needle tube accommodation hole 42. However, as is the case with a needle-equipped outer cylinder 1a of an example illustrated in FIG. 15, an outer cylinder member 2a may be provided with the needle tube locking portion 29. In the outer cylinder 1a of this example, a joining member 4a does not have a needle tube locking portion. An opening diameter of a proximal end opening of the joining member 4a is larger than an outer diameter of the proximal end 33 of the needle tube 3, and the needle tube 3 inserted into the joining member 4a penetrates the joining member 4a and the proximal end 33 thereof projects from the proximal end opening of the joining member 4a. The needle tube locking portion 29 is provided on the proximal end of the inner cavity 26 of the outer cylinder member 2a, and the projecting proximal end 33 of the needle tube 3 abuts the needle tube locking portion 29, so that further movement in the proximal end direction is restricted. Therefore, a projecting length of the needle tube 3 from a distal end of the outer cylinder member 2a is constant.

In this example, the needle tube locking portion 29 is formed of an annular projection that projects from an inner surface of the proximal end portion of the inner cavity 26 of the outer cylinder member 2a. Also, the annular projection having the rising surface directed in the distal end direction with respect to the inner surface of the inner cavity 26 is preferable. By such configuration, an abutment state with the proximal end 33 of the needle tube 3 is stabilized. However, the needle tube locking portion 29 may also be provided with, for example, an inclined surface a diameter of which is reduced in the proximal end direction. The needle tube locking portion 29 may also be one or a plurality of ribs that is not annular. In this example, the needle tube locking portion 29 is provided on the proximal end of the inner cavity 26. However, the needle tube locking portion 29 may also be located not on the proximal end of the inner cavity 26 but distal of the proximal end by a predetermined length.

Figure 16:
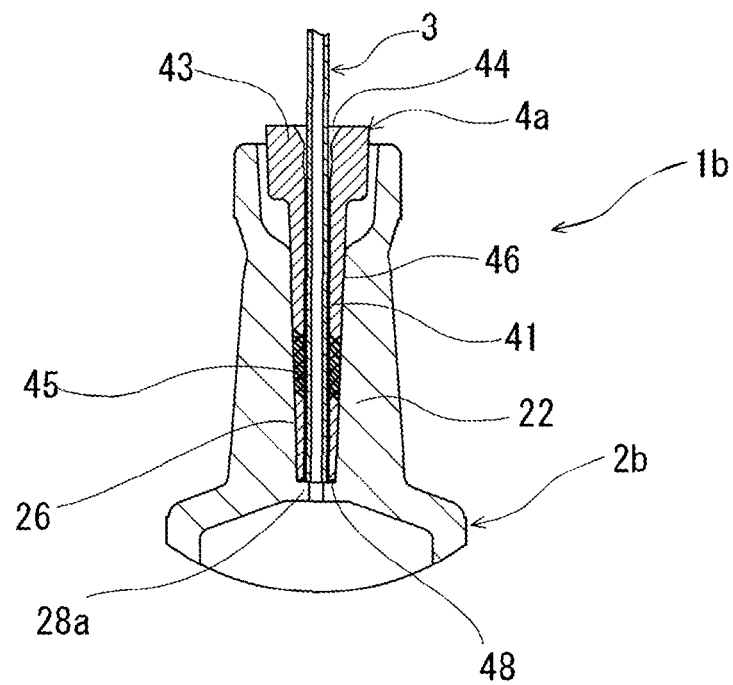
FIG. 16 is an enlarged longitudinal cross-sectional view of the distal end portion of the needle-equipped outer cylinder according to another example according to an embodiment of the present invention.

Furthermore, as is the case with a needle-equipped outer cylinder 1b of an example illustrated in FIG. 16, a projection 28a provided on the proximal end portion of the inner cavity 26 of an outer cylinder member 2b may abut the abutment portion 48 of a proximal end portion of the joining member 4a and also abut the proximal end 33 of the needle tube 3. In this case, a projecting height of the projection 28a is higher than that of the projection 28 of the outer cylinder 1a described above.

Although the example in which the shape of the outer cylinder main body 21 is formed into a substantially cylindrical shape is described in this embodiment, the shape of the outer cylinder main body 21 may also be a hollow square pole shape or hexagonal column shape.

A material compatible with the forming material of the joining member 4 to be used is preferably selected as the material of the outer cylinder member 2.

In particular, as described below, the distal end joint 22 of the outer cylinder member 2 and the joining member 4 are fixedly joined to each other by heat-welding. Therefore, the material of the outer cylinder member 2 and the material of the joining member 4 are preferably substantially the same material. As a result, it is possible to obtain an excellent joining property between the distal end joint 22 and the joining member 4 and to firmly fix the distal end joint 22 and the joining member 4. In addition, because a welded portion between the distal end joint 22 and the joining member 4 may be made less noticeable, an appearance of the needle-equipped outer cylinder 1 may be improved.

Such needle tube 3, joining member 4, and outer cylinder member 2 are welded by a manufacturing method (described below) to form the needle-equipped outer cylinder 1 as illustrated in FIGS. 1 to 4. As illustrated in FIG. 4, the needle-equipped outer cylinder 1 includes the heat-welded portion 45 formed in the position on the proximal end side by a predetermined length from the distal end of the distal end joint 22 of the outer cylinder member 2. The joining outer peripheral portion of the joining member 4 is melted and solidified in the position on the proximal end side by a predetermined length from the distal end of the distal end joint 22 of the outer cylinder member 2, so that the heat-welded portion 45 is formed. The joining member 4 is joined to the inner peripheral surface of the distal end joint 22 of the outer cylinder member 2 on the outer peripheral portion of the heat-welded portion 45, and is fixedly joined to the outer peripheral surface of the needle tube 3 on the inner peripheral portion of the heat-welded portion 45. In the outer cylinder of the present embodiment, the heat-welded portion 45 and the vicinity thereof do not contain air bubbles. Therefore, there is no fragile portion due to the air bubbles.

In a site on the distal end side of the heat-welded portion 45, the distal end joint 22 includes a non-welded abutment portion 46 that is not heat-welded to the joining member 4 but abuts the joining member 4. In this manner, the distal end joint 22 includes the non-welded abutment portion 46 for heating to weld only a site closer to the joining outer peripheral portion 47 of the joining member 4 such that a site closer to the distal end of the joining member 4 is not softened to be deformed as described below.

The non-welded abutment portion 46 in the outer cylinder desirably has residual strain and does not have crack. The one including the non-welded abutment portion 46 that is not heat-welded to the joining member 4 but abuts the joining member 4 in which the non-welded abutment portion 46 has residual strain and does not have the crack may be manufactured by a method for manufacturing the needle-equipped outer cylinder to be described below.

Furthermore, the non-welded abutment portion 46 preferably has a phase difference in birefringence measurement due to residual strain, and frequency of occurrence of the phase difference exceeding 800 nm in the birefringence measurement preferably is 1/10 or smaller of the frequency of occurrence of the phase difference smaller than 800 nm. Also, in another representation, it is preferable that an area in which the phase difference is 800 nm or larger in a predetermined area portion of a vertical cross-section of the outer cylinder in the non-welded abutment portion 46 is 10% or smaller.

Herein, as the "phase difference", an in-plane birefringence phase difference per unit thickness with respect to incident light in a radial direction of the distal end joint 22 in the site of the non-welded abutment portion 46 is used. The phase difference is obtained by using two types of characteristic data: (i) data of a retardation (birefringence phase difference) characteristic Re measured by a two-dimensional birefringence measurement device, and (ii) surface distribution data of an axis (fast axis, slow axis) angle. The phase difference (in-plane phase difference) may be measured using a commercially available phase difference measurement device (for example, "WPA-100" manufactured by Photonic Lattice and "KOBRA-21 ADH" manufactured by Oji Scientific Instruments) or the Senarmont method.

If the frequency of occurrence of the phase difference exceeding 800 nm in the birefringence measurement is not larger than 1/10 of the frequency of occurrence of the phase difference smaller than 800 nm, the non-welded abutment portion 46 has residual strain but does not have a portion with significant strain (for example, the crack or a portion that later causes a crack).

It is preferable that the non-welded abutment portion 46 be free from occurrence of the phase difference exceeding 900 nm in the birefringence measurement. In another representation, it is preferable that an area in which the phase difference is 900 nm or larger in a predetermined area portion of the vertical cross-section of the outer cylinder in the non-welded abutment portion 46 is substantially 0. Furthermore, it is preferable that the non-welded abutment portion 46 has a peak of occurrence frequency of the phase difference in the birefringence measurement in a range of 100 nm to 500 nm.

Next, a prefilled syringe 10 using the needle-equipped outer cylinder 1 according to an embodiment of the present invention is described.

The prefilled syringe 10 of the present embodiment is provided with the needle-equipped outer cylinder 1 described above, medicine solution 12 filled in the outer cylinder main body 21 of the outer cylinder 1, a gasket 5 accommodated in the outer cylinder main body 21 and slidable in the outer cylinder main body 21, and a cap 6 attached to the distal end portion of the needle-equipped outer cylinder 1 to seal the needle tip 33 of the needle tube 3.

As illustrated in FIG. 10, the syringe 10 is provided with the needle-equipped outer cylinder 1 described above, the cap 6 attached to the distal end portion of the needle-equipped outer cylinder 1 to seal the needle tip 32 of the needle tube 3, the gasket 5 accommodated in the outer cylinder main body 21 of the needle-equipped outer cylinder 1 and slidable in the outer cylinder main body 21, and a plunger 7 attached to the gasket 5. The plunger 7 is provided with a main body 71, a gasket attaching portion 72 formed on a distal end of the main body 71, and a pressing portion 73 provided on a proximal end portion. The gasket is also provided with a plunger attaching portion that receives the gasket attaching portion 72 of the plunger 7 to engage with the same. The syringe 10 of this example is a prefilled syringe in which the outer cylinder main body 21 of the needle-equipped outer cylinder 1 is filled with the medicine solution 12.

The cap 6 is formed into a cylindrical shape, a base 61 side in the axial direction is opened, and a distal end in the axial direction is closed. The cap 6 is formed of, for example, an elastic member such as rubber or an elastomer. The cap 6 is attached to the distal end joint 22 of the outer cylinder member 2 so as to cover the needle tip 32 of the needle tube 3 and the distal end joint 22 of the outer cylinder member 2. As illustrated in FIG. 11, the needle tube 3 side and the distal end joint 22 are inserted into an inner cavity 62 of the cap 6. Furthermore, in this example, the cap 6 is provided with a cylindrical covering member 8 attached to an outer side of the cap 6 and engaging with the cap 6.

Note that, an inner diameter of the inner cavity 62 of the cap 6 is formed to be substantially equal to an outer diameter of a distal end side fitting portion (distal end side enlarged diameter portion) 25 of the distal end joint 22 or slightly smaller than the distal end side fitting portion 25. Therefore, when the cap 6 is attached to the distal end joint 22, an outer peripheral surface of the distal end side fitting portion 25 is brought into close contact with an inner peripheral surface of the cap 6. Therefore, a space covering the needle tube 3 projecting from the joining member 4 is sealed by the distal end side fitting portion 25 and the inner peripheral surface of the cap 6. By configuring in this manner, it is possible to prevent bacteria from adhering to the needle tip 32. Also, at the same time, a needle tip holding portion 63 holds the needle tip 32.

The inner peripheral surface of the cap 6 tightens a constricted portion at a boundary between the distal end side fitting portion (distal end side enlarged diameter portion) 25 and a tapered fitting portion (joining member receiving portion) 24 in the distal end joint 22 by an elastic force thereof. In this manner, the inner peripheral surface of the cap 6 and the constricted portion of the distal end joint 22 engage with each other, and the cap 6 may be prevented from being detached from the distal end joint 22 during conveyance.

Next, the method for manufacturing the needle-equipped outer cylinder 1 is described.

The method for manufacturing the needle-equipped outer cylinder of the present embodiment is the method for manufacturing the outer cylinder formed of the needle tube 3, the joining member 4 including the needle tube accommodation hole 42 penetrating from the distal end to the proximal end for accommodating the proximal end side portion of the needle tube 3 and the joining outer peripheral portion 47 the outer diameter of which is reduced from the distal end side toward the proximal end side, and the outer cylinder member 2 provided with the distal end joint 22 including the inner cavity 26 capable of receiving the joining outer peripheral portion 47 of the joining member 4 from the distal end side.

In the method for manufacturing the needle-equipped outer cylinder according to the present embodiment, as the outer cylinder member 2, that provided with the projection 28 provided on the proximal end portion of the inner cavity 26 is used, and as the joining member 4, that provided with the abutment portion 48 that abuts the projection 28 of the outer cylinder member 2 is used.

In the method for manufacturing the needle-equipped outer cylinder according to the present embodiment, an assembling step at which the needle tube 3 is inserted into or inserted to be fixed to the needle tube accommodation hole 42 of the joining member 4, the joining member 4 is inserted into the distal end joint 22 of the outer cylinder member 2, and the projection 28 of the outer cylinder member 2 abuts the abutment portion 48 of the joining member 4, and a joining member welding step at which the joining member 4 is heat-welded to the distal end joint 22 of the outer cylinder member 2 while pressing the distal end portion of the joining member 4 in the proximal end direction of the joining member 4 by a pressing member are performed.

In order to manufacture the needle-equipped outer cylinder 1 of the present embodiment, as illustrated in FIG. 9, the needle tube 3, the joining member 4, and the outer cylinder member 2 are prepared. The needle tube 3 is formed as a desired tubular body by, for example, pressing of flat metal or swaging of a hollow pipe. The joining member 4 and the outer cylinder member 2 are formed by injection molding. In this manner, by separately molding the joining member 4 and the outer cylinder member 2, a mold may be made compact and simplified.

Next, the assembling step of the needle tube 3 and the joining member 4 to the outer cylinder member is performed.

At this assembling step, the joining member 4 is inserted into the tapered inner cavity 26 of the distal end joint 22 of the outer cylinder member 2. When the joining member 4 is pushed to the proximal end in the distal end joint 22, the projection 28 of the outer cylinder member 2 abuts the abutment portion 48 of the joining member 4. Note that, in this example, because the inner cavity 26 in the distal end joint 22 of the outer cylinder member 2 is the tapered inner cavity 26, the proximal end side cylinder portion 41 and the joining outer peripheral portion (tapered portion) 47 of the joining member 4 are brought into a state taper fitted to the tapered inner cavity 26 of the distal end joint 22 or nearly tapered fitted.

The needle tube 3 is inserted. At this inserting step, the needle tube 3 is inserted from the proximal end side into the needle tube accommodation hole 42 of the joining member 4, and the needle tube 3 is assembled to the joining member 4 attached to the outer cylinder member 2. Note that, it is also possible that the needle tube 3 is not inserted into the joining member 4 after the attachment of the joining member 4 to the outer cylinder member 2, but the needle tube 3 is inserted to be fixed to the joining member 4 in advance before the attachment of the joining member 4 to the outer cylinder member 2. Alternatively, the needle tube 3 and the joining member 4 may be integrally molded in advance by insert molding.

Figure 12:
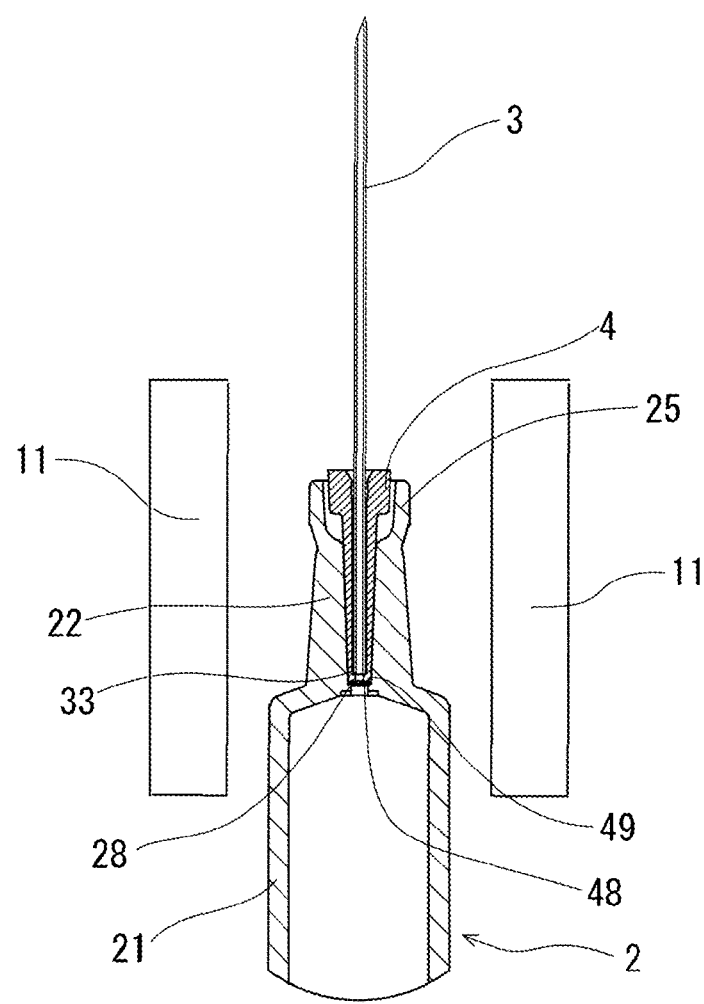
FIG. 12 is an illustrative view for illustrating a preheating step in a method for manufacturing the needle-equipped outer cylinder according to an embodiment of the present invention.

In this example, as illustrated in FIGS. 4 and 12, the joining member 4 provided with the needle tube locking portion 49 provided on the proximal end portion of the needle tube accommodation hole 42 is used. Therefore, the proximal end 33 of the needle tube 3 inserted into the joining member 4 abuts the needle tube locking portion 49, and movement in the proximal end direction, in other words, removal from the joining member 4 is restricted.

It is preferable to perform a preheating step after the assembling step described above and before the joining member welding step to be described below.

At the preheating step, heating to temperature equal to or lower than a softening point of the forming material of the outer cylinder member 2 is preferable. It is preferable to heat to temperature near a glass transition point of the forming material of the outer cylinder member 2 or higher and the softening point or lower. Specifically, in a case of using the outer cylinder member 2 made of cyclic polyolefin (COP) as the forming material, the needle-equipped outer cylinder 1 after the above-described inserting step is preferably heated so as to be within a heating range of 110° C. to 150° C.

As a heating means, as illustrated in FIG. 12, it is preferable to use two halogen heaters 11 arranged so as to be opposite to each other with the outer cylinder member 2 interposed therebetween. The use of the halogen heater 11 facilitates local heating of the non-welded abutment portion 46 of the outer cylinder member 2 described above. In addition, an arrival speed in a depth direction may be increased. As for an example of the above-described needle-equipped outer cylinder 1, the preheating step in a short time of 100 W (12 V)×2 seconds (S) is possible in order to heat to the above-described heating range. At the preheating step, a periphery of the distal end joint 22 of the outer cylinder member 2 may be uniformly heated by rotating the needle-equipped outer cylinder 1 about its axis. Note that, although the preheating step is performed on the non-welded abutment portion 46 in this embodiment, the preheating step may also be performed on other sites in which the crack might occur. Alternatively, the preheating step may be performed on the entire distal end joint 22.

Also, the heating means is not limited to the above-described halogen heater 11, but a means such as a carbon heater and a hot air may also be used. For example, in a case in which the needle-equipped outer cylinder 1 is heated with hot air in a booth, for example, in the needle-equipped outer cylinder 1 having the same configuration as that described above, heating is performed at 290° C.×6 seconds (S) in the booth to 110° C. to 150° C.

Figure 13:
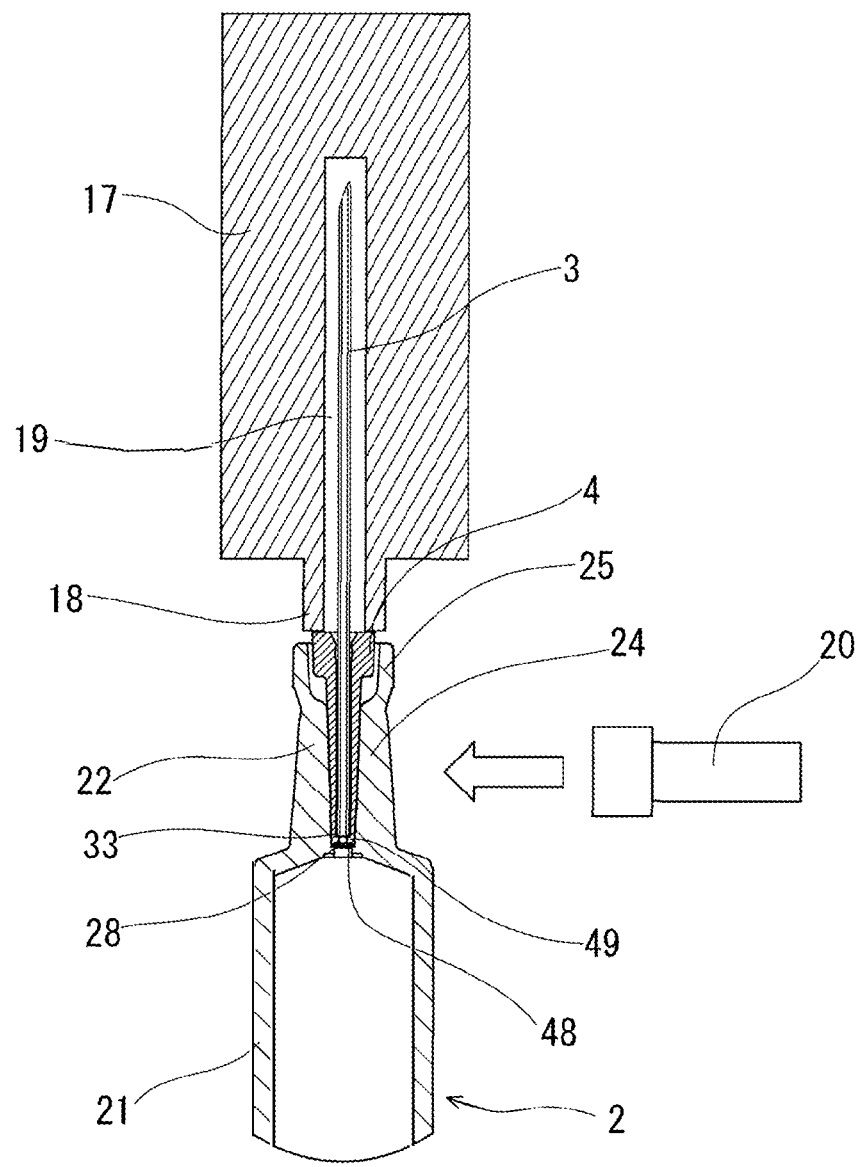
FIG. 13 is an illustrative view for illustrating a joining member welding step in the method for manufacturing the needle-equipped outer cylinder according to an embodiment of the present invention.

Next, after the above-described preheating step, the joining member welding step is performed. As illustrated in FIG. 13, the joining member welding step is performed by heat-welding the joining member 4 to the distal end joint of the outer cylinder member 2 while pressing the distal end side cylinder portion (distal end portion) 43 of the joining member 4 in the proximal end direction of the joining member 4 by a pressing member 17. The pressing is preferably performed while pressing with a pressing force of 4N to 30N in the proximal end direction of the joining member 4.

As described above, the tapered inner cavity 26 of the outer cylinder member 2 and the joining outer peripheral portion (tapered portion) 47 of the joining member 4 are in a state taper fitted or nearly taper fitted in the joining member 4 inserted into the distal end joint 22 of the outer cylinder member 2 and in a state in which the projection 28 of the outer cylinder member 2 abuts the abutment portion 48 of the joining member 4. In this state, the heat-welding is performed.

The pressing member 17 includes an accommodation hole 19 for accommodating the needle tube 3 and a pressing portion 18 for pressing the distal end side cylinder portion 43 of the joining member 4. When pressure is applied to the joining member 4 by the pressing portion 18, the projection 28 of the outer cylinder member 2 abuts the abutment portion 48 of the joining member 4, so that the pressing force is surely transmitted to the abutment portion of the joining member 4. At the joining member welding step, a state of the outer peripheral surface of the joining outer peripheral portion 47 and the tapered inner cavity 26 may be maintained. By heating and partial melting of the joining member 4, the joining member is surely fixedly joined to the outer cylinder member. In this example, because both the joining outer peripheral portion 47 of the joining member 4 and the inner cavity 26 of the outer cylinder member 2 are tapered, a force to axially compress the resin melted at the time of heating acts, so that the heat-welding may be surely performed.

In this embodiment, the heat-welding is generated using a semiconductor laser irradiation device 20. The semiconductor laser irradiation device 20 applies a laser to the heat-welded portion 45 between the joining outer peripheral portion 47 of the joining member 4 and the tapered inner cavity 26 of the outer cylinder member 2. As a result, the needle tube 3 generates heat and the joining member 4 is heated. The joining member 4 is softened and adheres to the needle tube 3 and the distal end joint 22 of the outer cylinder member 2. As a result, the joining member 4 and the needle tube 3, and the joining member 4 and the distal end joint 22 of the outer cylinder member 2 are fixedly joined by heat-welding, and the needle-equipped outer cylinder 1 is manufactured.

Note that, an irradiation range of the semiconductor laser irradiation device is determined such that only a predetermined range of the heat-welded portion 45 closer to the proximal end of the joining member 4 is melted so as to prevent the proximal end side cylinder portion 41 of the joining member 4 from softening and having a larger outer diameter than the inner diameter of the opening of the tapered inner cavity 26 and to bring the surfaces of the joining outer peripheral portion 47 and the tapered inner cavity 26 into close contact with each other by the pressing member 17. At that time, the laser irradiates a thin portion between ribs of the tapered fitting portion 24.

Also, the heat-welded portion 45 may be set in an arbitrary position, thereby controlling flexibility (deflection) of the needle tube. For example, in a case in which occurrence of kink (break) is prevented by making the needle tube easy to bend, the heat-welded portion 45 is preferably provided from the vicinity of an intermediate portion to the vicinity of a proximal end of the tapered fitting portion 24 or from the vicinity of an intermediate portion to the vicinity of the proximal end of the joining member 4, and in a case in which the deflection is not preferred, the heat-welded portion 45 is preferably provided from the vicinity of the intermediate portion to the vicinity of a distal end of the tapered fitting portion 24 or from the vicinity of the intermediate portion to the vicinity of the distal end of the joining member 4.

Note that, in a case in which a thickness of the joining member 4 is set to 0.38 to 0.48 mm, and a thickness of a portion without the ribs of the tapered fitting portion 24 of the outer cylinder is set to 0.8 to 1.1 mm, an output of the semiconductor laser irradiation device 20 is preferably set to 5 to 20 W, and an irradiation time of the laser is preferably set to 1.5 to 2.0 seconds (S). Also, as for the optical system, it is preferable to set a focal diameter to $\varphi$ 3.0 to 3.5 mm. The above-described conditions are those of a case in which cyclic polyolefin (COP) is applied as the material of the joining member; it is required to set the condition to obtain appropriate resin temperature in accordance with a characteristic of the resin to be used such that foaming, resin burning, and deformation do not occur. In this embodiment, the joining member 4 and the needle tube 3, and the joining member 4 and the outer cylinder member 2 are joined by using the semiconductor laser irradiation device 20, so that it is possible to fix the needle tube 3 to the outer cylinder member 2 without using an adhesive.

Figure 14:
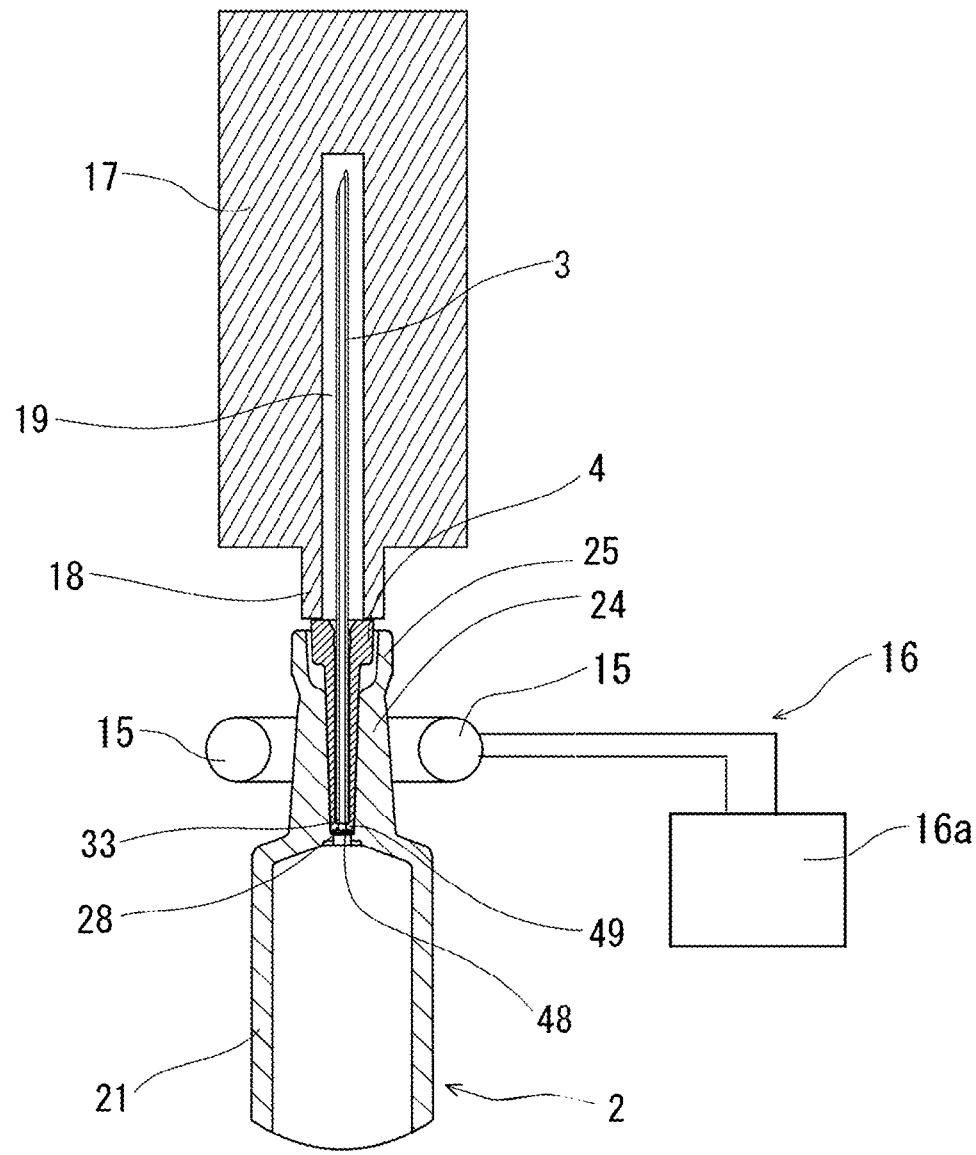
FIG. 14 is an illustrative view for illustrating a preheating step in a method for manufacturing a needle-equipped outer cylinder according to another embodiment according to an embodiment of the present invention.

It is also possible to use not only the semiconductor laser irradiation device 20 at the joining member welding step of the above-described embodiment but also another welding means. For example, as in another embodiment illustrated in FIG. 14, a high-frequency induction heating device 16 may be used to cause the heat-welding. The high-frequency induction heating device 16 is provided with a work coil 15 and a power supply 16a for applying alternating current to the work coil 15. When the alternating current is applied from the power supply 16a to the work coil 15, a magnetic field is generated around the work coil 15, and eddy current is generated in the needle tube 3. As a result, the needle tube 3 generates heat and the joining member 4 is heated. The joining member 4 is softened and adheres to the needle tube 3 and the distal end joint 22 of the outer cylinder member 2. As a result, the joining member 4 and the needle tube 3, and the joining member 4 and the distal end joint 22 of the outer cylinder member 2 are fixedly joined by heat-welding, and the needle-equipped outer cylinder 1 is manufactured.

Also, in the above-described embodiment, the outer cylinder member 2 and the joining member 4 are of substantially the same material. Substantially the same materials have good compatibility. Note that the materials of the outer cylinder member 2 and the joining member 4 may be different thermoplastic resins having compatibility at the time of melting. To have the compatibility means that thermodynamic mutual solubility is excellent, in other words, this means that both are not separated after curing.

Also, in the above-described embodiment, the outer cylinder member of the needle-equipped outer cylinder is a syringe outer cylinder member that may be filled with the medicine solution. Note that the outer cylinder member of the needle-equipped outer cylinder may be a needle hub member attachable to a nozzle portion provided on a distal end portion of a syringe outer cylinder that may be filled with the medicine solution. In this case, the needle hub member includes an attaching portion that may be attached to the nozzle portion of the syringe outer cylinder on a proximal end portion thereof. The needle-equipped outer cylinder using such needle hub member may also be used for tapping the needle tip of the needle tube from the surface of the skin and injecting the medicine solution filled in the syringe outer cylinder into the living body.

In addition, the needle-equipped outer cylinder of the present embodiment may be manufactured using the needle tube and the joining member integrally molded in advance by insert molding. In this case also, the joining outer peripheral portion of the joining member is melted and solidified in the position on the proximal end side by a predetermined length from the distal end of the distal end joint of the outer cylinder member at the joining member welding step, so that the heat-welded portion is formed. The joining member is fixedly joined to the inner peripheral surface of the distal end joint of the outer cylinder member by the outer peripheral portion of the heat-welded portion, and is fixedly joined to the outer peripheral surface of the needle tube by the inner peripheral portion of the heat-welded portion. Note that, in this case, the joining member is a part other than the heat-welded portion of the joining outer peripheral portion A needle-equipped outer cylinder according to an embodiment of the present invention is configured as follows.

(1) A needle-equipped outer cylinder provided with: a needle tube; a joining member including a needle tube accommodation hole for accommodating a proximal end side portion of the needle tube and a joining outer peripheral portion provided on an outer peripheral portion of the needle tube accommodation hole; and an outer cylinder member provided with a distal end joint including an inner cavity capable of receiving the joining outer peripheral portion of the joining member from a distal end side, in which the needle tube accommodation hole penetrates the joining member from a distal end of the joining member to a proximal end of the joining member, the outer cylinder member is provided with a projection provided on a proximal end portion of the inner cavity and projecting in the inner cavity, the joining member is provided with an abutment portion that abuts the projection of the outer cylinder member on a proximal end portion of the joining member, at least the joining outer peripheral portion of the joining member is inserted into the inner cavity of the distal end joint of the outer cylinder member, and the abutment portion of the joining member abuts the projection of the outer cylinder member, and the joining outer peripheral portion of the joining member includes a heat-welded portion formed in a position on a proximal end side by a predetermined length from a distal end of the distal end joint of the outer cylinder member, the joining outer peripheral portion of the joining member is fixedly joined to an inner peripheral surface of the distal end joint on an outer peripheral portion of the heat-welded portion and is fixedly joined to an outer peripheral surface of the needle tube on an inner peripheral portion of the heat-welded portion.

This needle-equipped outer cylinder in which the joining member is fixedly joined to the outer cylinder member excellently may be used effectively.

Also, the above-described embodiment may be as follows.

(2) The needle-equipped outer cylinder according to (1) described above, in which the abutment portion of the joining member is formed of a rib extending in a proximal end direction formed on the proximal end of the joining member.

(3) The needle-equipped outer cylinder according to (1) described above, in which the abutment portion of the joining member is formed of a proximal end surface of the joining member.

(4) The needle-equipped outer cylinder according to any one of (1) to (3) described above, in which the joining member is provided with a needle tube locking portion provided on a proximal end portion of the needle tube accommodation hole to lock a proximal end of the needle tube.

(5) The needle-equipped outer cylinder according to any one of (1) to (3) described above, in which the outer cylinder member is provided with a needle tube locking portion provided on the proximal end portion of the inner cavity to lock a proximal end of the needle tube.

(6) The needle-equipped outer cylinder according to any one of (1) to (5) described above, in which the joining outer peripheral portion of the joining member is a tapered portion an outer diameter of which is reduced from a distal end toward a proximal end of the joining outer peripheral portion, and the inner cavity of the outer cylinder member is a tapered inner cavity a diameter of which is reduced toward a proximal end of the outer cylinder member.

(7) The needle-equipped outer cylinder according to any one of (1) to (6) described above, in which the distal end joint of the outer cylinder includes a non-welded abutment portion that is not heat-welded to the joining member but abuts the joining member in a site on a distal end side of the heat-welded portion of the joining member, and the non-welded abutment portion has residual strain but no crack.

(8) The needle-equipped outer cylinder according to any one of (1) to (7) described above, in which a forming material of the joining member and a forming material of the outer cylinder member are thermoplastic resins having compatibility at the time of melting.

(9) The needle-equipped outer cylinder according to any one of (1) to (8) described above, in which the outer cylinder member is a syringe outer cylinder member including an outer cylinder main body capable of being filled with medicine solution.

(10) The needle-equipped outer cylinder according to any one of (1) to (8) described above, in which the outer cylinder member is a needle hub member including an attaching portion attachable to a nozzle portion provided on a distal end portion of a syringe outer cylinder.

A prefilled syringe according to an embodiment of the present invention is configured as follows.

(11) A prefilled syringe provided with: the needle-equipped outer cylinder according to (9) described above; the medicine solution filled in the outer cylinder main body; a gasket accommodated in the outer cylinder main body and slidable in the outer cylinder main body; and a cap attached to a distal end portion of the needle-equipped outer cylinder to seal a needle tip of the needle tube.

This prefilled syringe in which the joining member is fixedly joined to the outer cylinder member excellently also may be used effectively.

A method for manufacturing a needle-equipped outer cylinder according to an embodiment of the present invention is performed as follows.

(12) A method for manufacturing a needle-equipped outer cylinder provided with a needle tube, a joining member including a needle tube accommodation hole for accommodating the needle tube and a joining outer peripheral portion provided on an outer peripheral portion of the needle tube accommodation hole, and an outer cylinder member provided with a distal end joint including an inner cavity capable of receiving the joining outer peripheral portion of the joining member, the method for manufacturing the needle-equipped outer cylinder provided with:

a preparing step of preparing the outer cylinder member provided with a projection projecting in the inner cavity on a proximal end portion of the inner cavity, the joining member provided with an abutment portion that abuts the projection of the outer cylinder member on a proximal end portion, and the needle tube;

an assembling step of assembling the needle tube, the joining member, and the outer cylinder member such that the needle tube is inserted into or inserted to be fixed to the needle tube accommodation hole of the joining member, the joining member is inserted into the distal end joint of the outer cylinder member, and the abutment portion of the joining member abuts the projection of the outer cylinder member; and a welding step of heat-welding the joining outer peripheral portion of the joining member to an inner peripheral surface of the distal end joint of the outer cylinder member and an outer peripheral surface of the needle tube by allowing the needle tube to generate heat by a heat generating device to allow the needle tube to generate heat while pressing a distal end portion of the joining member in a proximal end direction of the joining member by a pressing member.

In this manufacturing method, the joining member is heat-welded to the distal end joint of the outer cylinder member while pressing the distal end portion of the joining member in the proximal end direction of the joining member by the pressing member in a state in which a lower end of the joining member abuts the projection provided on the proximal end portion of the inner cavity of the outer cylinder member, so that it is possible to apply sufficient pressure to the melted resin and the joining member is fixedly joined to the outer cylinder member excellently.

Also, the above-described embodiment may be as follows.

(13) The method for manufacturing the needle-equipped outer cylinder according to (12) described above, in which the joining member is provided with a needle tube locking portion provided on a proximal end portion of the needle tube accommodation hole for locking a proximal end of the needle tube, and locks the proximal end of the needle tube inserted into the needle tube accommodation hole of the joining member at the assembling step by the needle tube locking portion.

(14) The method for manufacturing the needle-equipped outer cylinder according to (12) or (13) described above, in which a forming material of the joining member and a forming material of the outer cylinder member are thermoplastic resins having compatibility at the time of melting.

The invention claimed is:
1. A needle-equipped outer cylinder comprising:
  a needle tube;
  a joining member comprising:
    a needle tube accommodation hole that accommodates a proximal end side portion of the needle tube and penetrates the joining member from a distal end of the joining member to a proximal end of the joining member,
    a joining outer peripheral portion provided on an outer peripheral portion of the needle tube accommodation hole,
    an abutment portion located at a proximal end portion of the joining member, the abutment portion comprising a rib formed on the proximal end portion of the joining member and extending in a proximal end direction; and
  an outer cylinder member comprising:
    a distal end joint that comprises an inner cavity that receives the joining outer peripheral portion of the joining member from a distal end side of the inner cavity, and
    a projection located at a proximal end portion of the inner cavity and projecting into the inner cavity,
  wherein the abutment portion abuts the projection of the outer cylinder member, and
  wherein the joining outer peripheral portion of the joining member comprises a heat-welded portion formed at a position proximal of a distal end of the distal end joint, and
  wherein the joining outer peripheral portion of the joining member is fixedly joined to an inner peripheral surface of the distal end joint on an outer peripheral portion of the heat-welded portion and is fixedly joined to an outer peripheral surface of the needle tube on an inner peripheral portion of the heat-welded portion.

2. The needle-equipped outer cylinder according to claim 1, wherein the joining member comprises a needle tube locking portion on a proximal end portion of the needle tube accommodation hole to lock a proximal end of the needle tube.

3. The needle-equipped outer cylinder according to claim 1, wherein the outer cylinder member comprises a needle tube locking portion provided on the proximal end portion of the inner cavity to lock a proximal end of the needle tube.

4. The needle-equipped outer cylinder according to claim 1, wherein the joining outer peripheral portion of the joining member is a tapered portion, an outer diameter of which is reduced from a distal end toward a proximal end of the joining outer peripheral portion, and the inner cavity of the outer cylinder member is a tapered inner cavity, a diameter of which is reduced toward a proximal end of the outer cylinder member.

5. The needle-equipped outer cylinder according to claim 1, wherein the distal end joint of the outer cylinder comprises a non-welded abutment portion that is not heat-welded to the joining member but abuts the joining member in a site on a distal end side of the heat-welded portion of the joining member, and the non-welded abutment portion has residual strain but no crack.

6. The needle-equipped outer cylinder according to claim 1, wherein the joining member the outer cylinder member are formed of thermoplastic resins having compatibility at the time of melting.

7. The needle-equipped outer cylinder according to claim 1, wherein the outer cylinder member is a syringe outer cylinder member comprising an outer cylinder main body configured to be filled with medicine solution.

8. A prefilled syringe comprising:
  the needle-equipped outer cylinder according to claim 7;
  the medicine solution filled in the outer cylinder main body;
  a gasket accommodated in the outer cylinder main body and slidable in the outer cylinder main body; and
  a cap attached to a distal end portion of the needle-equipped outer cylinder to seal a needle tip of the needle tube.

9. A method for manufacturing a needle-equipped outer cylinder, the method comprising:
  providing a needle tube;
  providing a joining member comprising:
    a needle tube accommodation hole for accommodating the needle tube,
    a joining outer peripheral portion provided on an outer peripheral portion of the needle tube accommodation hole, and
    an abutment portion located at a proximal end portion of the joining member, the abutment portion comprising a rib formed on the proximal end portion of the joining member and extending in a proximal end direction;
  providing an outer cylinder member comprising:
    a distal end joint that comprises an inner cavity configured to receive the joining outer peripheral portion of the joining member, and
    a projection located at a proximal end portion of the inner cavity and projecting into the inner cavity;
  assembling the needle tube, the joining member, and the outer cylinder member such that the needle tube is inserted into or inserted into and fixed to the needle tube accommodation hole of the joining member, the joining member is inserted into the distal end joint of the outer cylinder member, and the abutment portion of the joining member abuts the projection of the outer cylinder member; and
  heat-welding the joining outer peripheral portion of the joining member to an inner peripheral surface of the distal end joint of the outer cylinder member and an outer peripheral surface of the needle tube by causing the needle tube to generate heat by a heat generating device while pressing a distal end portion of the joining member in a proximal end direction of the joining member by a pressing member.

10. The method for manufacturing the needle-equipped outer cylinder according to claim 9, wherein the joining member comprises a needle tube locking portion on a proximal end portion of the needle tube accommodation hole, and, during the step of assembling, the needle tube locking portion locks the proximal end of the needle tube inserted into the needle tube accommodation hole of the joining member.

11. The method for manufacturing the needle-equipped outer cylinder according to claim 9, wherein the joining member and the outer cylinder member are formed of thermoplastic resins having compatibility at the time of melting.

* * * * *